United States Patent [19]

Riitano

[11] Patent Number: 4,609,352
[45] Date of Patent: Sep. 2, 1986

[54] RIGID DENTAL TOOL PROVIDED WITH INNER GUIDE CORE FOR CARRYING OUT THE REAMING AND RECTIFICATION OF DENTAL ROOT CANALS

[76] Inventor: Francesco Riitano, Via S. Giovanni Bosco, 11 - 88068 Soverato (Catanzaro), Italy

[21] Appl. No.: 609,145

[22] Filed: May 11, 1984

[30] Foreign Application Priority Data

May 25, 1983 [IT] Italy ................. 48369 A/83

[51] Int. Cl.⁴ ............................................. A61C 5/02
[52] U.S. Cl. ................................... 433/102; 433/165; 433/224
[58] Field of Search ................. 433/102, 81, 224, 165, 433/166

[56] References Cited

U.S. PATENT DOCUMENTS

| | | | |
|---|---|---|---|
| 2,773,501 | 12/1956 | Young | 433/81 |
| 2,878,809 | 3/1959 | Treace | 433/165 |
| 3,295,514 | 1/1967 | Hein | 433/81 |
| 3,534,476 | 10/1970 | Winters | 433/224 |
| 4,190,958 | 3/1980 | Martin | 433/102 |

FOREIGN PATENT DOCUMENTS

| | | | |
|---|---|---|---|
| 105840 | 1/1899 | Fed. Rep. of Germany | 433/224 |
| 1194061 | 11/1959 | France | 433/165 |
| 853645 | 11/1960 | United Kingdom | 433/165 |

*Primary Examiner*—John J. Wilson
*Attorney, Agent, or Firm*—Laff, Whitesel, Conte & Saret

[57] ABSTRACT

The present invention pertains to a rigid dental tool for carrying out the reaming and rectification of dental root canals and adapted to be operated either manually or through the use of dental hand held tools. The dental tool has two longitudinal portions with the first forming the attachment stem. The second is conical or cylindrical and extends from the first one through a frusto-conical connection piece. The second portion constitutes the working portion and is provided with cutting and-/or reaming means; which may be of a uniform type over the whole working portion or may comprise more types successively distributed along the working portion. The first and second portions are centrally provided with an inner longitudinal cavity that houses a freely rotating flexible core which projects an appropriate extent from the free end of the second portion, as required by the operation.

10 Claims, 6 Drawing Figures

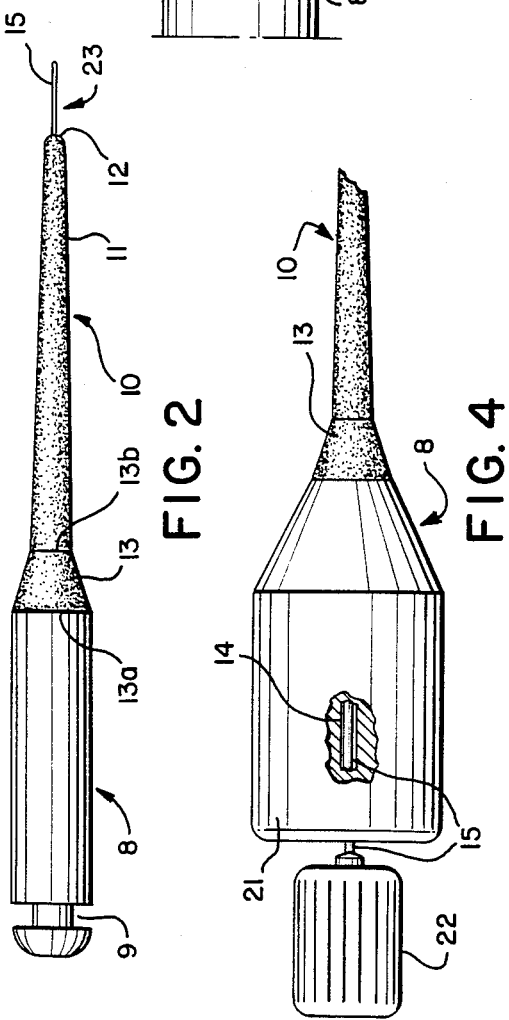
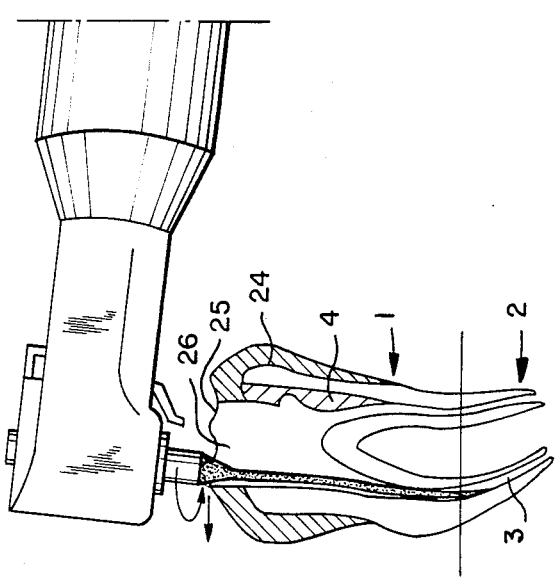
PRIOR ART FIG. 1
FIG. 3
FIG. 6
FIG. 2
FIG. 4
FIG. 5

RIGID DENTAL TOOL PROVIDED WITH INNER GUIDE CORE FOR CARRYING OUT THE REAMING AND RECTIFICATION OF DENTAL ROOT CANALS

BACKGROUND OF THE INVENTION

The present invention relates to a dental tool for carrying out the reaming and rectification of dental root canals by means of a manual operation or through the use of tools normally defined as dental hand held tools both of the mechanical and of the ultrasonic type.

DESCRIPTION OF THE PRIOR ART

Presently this is accomplished, after the chamber opening, by the flaring rectification of the first two thirds (globally indicated at 1 in FIG. 1) of the root canal 3, that is the elimination of the interferences 4 and the straightening of curved portions in canal 3, so as to achieve the alignment of the third coronal portion with the third middle portion of the root canal in order to facilitate the further penetration in the third apical portion thereof (globally indicated at 2 in FIG. 1) and its preparation before the beginning of the following operations for stopping the canal.

Though the operating steps are generally similar for all dental root canals, they are, however, very different according to the various teeth (upper and lower incisors, canines, molars and pre-molars). This difference concerns the diameter of the canals and the development of the canals. There are large and/or narrow canals and the canals may be either completely straight or curved or have rectilinear and curved portions. Their section may be circular, elliptic, kidney- or slit-shaped. In consideration of this, many canal tools have been used hitherto, which have imposed many operating passages as well as the necessity of adapting different methods for the individual morphology of the canals. This required long operating times for penetrating the canals above all the narrow and curved canals. Also, there were limitations inherent in the different tools, that became more rigid as their diameter increased and thus they could not follow the canal bendings. Furthermore, the increase in diameter and rigidity of the tools reduced ability of the tool to follow the bendings in canals 3 and many cause enlargements 5, thinning of the canal walls 6, formation of steps and flarings 7 (FIG. 1) and sometimes even the breaking of the walls themselves.

SUMMARY OF THE INVENTION

It is therefore an object of the present invention to provide a tool for carrying out the reaming, enlargement and reconstruction of root canals, which is particularly efficient in rectifying and straightening the first two thirds, while tending to cover the whole canal path, up to the apex and which can be utilized for the different types of canals.

Our tool has rigid reaming structure and is provided with a coaxial flexible core which is independent of the rotation of the tool's reaming portion so as to avoid the torsional stresses due to the reaming and therefore the risks of breaking the point and which is suitable to guide the progressive penetration of the rigid structure into the curved portions of the canal.

The flexible guide core, when provided with an operating end and when the tool is used manually, can be operated independently of the main tool, so that it carries out a previous enlargement of the canal or in any case ensures the practicability of the previously probed canal path, as the main tool moves forward towards the apex.

It is a further object of the invention to provide a tool suitable to be used both manually and through a dental hand tool, in which case said core is housed therein and partially engaged therewith, while being however removable and replaceable.

These and still further objects are achieved by the dental tool of the invention which, from a general point of view, is characterized in that it longitudinally consists of two portions, the first of them forming the attachment stem to a dental hand held tool or to a handle when manually operated and the second portion, extending from the first portion till the free end of the tool, forming the operating portion and supporting cutting and/or reaming means; the second portion, over the whole length thereof, and at least a part of the first portion being longitudinally and centrally provided with a cylindrical cavity housing a flexible core therein at least along a restricted and defined portion thereof, sliding freely and independent of the rotation of the tool, the core projects a maximum appropriate length from the free end of the second portion; the flexible guide core is removable and replaceable within the cylindrical cavity; the flexible guide core is engaged, close to its inner end, with the first portion adapted to be applied to a dental hand held tool or being freely fitted into the first portion adapted to be applied to a dental hand held tool or being freely fitted into the first portion and independently operated therein if applied to a handle for manual use of the tool.

Further features and advantages of the invention will become more apparent from the detailed description of a preferred embodiment given hereinafter by way of example only, with reference to the accompanying drawings.

BRIEF DESCRIPTION OF THE DRAWINGS

FIG. 1 illustrates a dental tool and a cut-away tooth;

FIG. 2 is a side view of the dental tool of the present invention;

FIG. 3 is a partial side view of the dental tool of the present invention with its cylindrical operating portion being half-sectioned close to the end of the central cavity;

FIG. 4 is a partial side view of another embodiment of the dental tool of the present invention;

FIG. 5 is a side view of another embodiment of the dental tool of the present invention;

FIG. 6 is a diagrammatic view of the dental tool of the present invention attached to a dental hand held tool.

DESCRIPTION OF THE PREFERRED EMBODIMENTS OF THE INVENTION

Referring to the drawings, FIG. 2 shows a side view of the tool according to the invention, having as to its longitudinal extension, two portions. The first portion 8 is substantially cylindrical and constitutes the common attachment stem to a dental hand held tool, through common fitting means, for example a peripheral groove 9. The second portion 10, forms the operating portion of the tool and has thereon common cutting and/or reaming means 11.

The second operating portion 10 extends from the first portion 8 up to the end of the tool where it terminates in a free end 12.

The joining section between the first portion 8 and the second operating portion 10 is a frusto-conical connection piece 13 whose base of bigger diameter 13a corresponds to the lower section of the first portion 8 and whose base of smaller diameter 13b corresponds to the upper section of the second operating portion 10; cutting means 11 may be applied to the connection piece 13 or is thereon.

According to two different embodiments derived from the necessity of adapting the tool to the different anatomical morphologies of the root canals 3, the second operating portion 10, starting from the upper section 13b thereof, has a quite cylindrical form up to the free end 12 (FIG. 3) or, starting from section 13b, a quite conical form the diametral section of which gradually decreases up to the free end 12 (FIGS. 2, 4 and 5). The first and second portions 8 and 10 respectively, starting from end 12, are provided with a centrally and longitudinally extending cylindrical cavity 14 housing a flexible core 15 inside it. The flexible core is limitedly slidable in a longitudinal way completely independent of the rotation of the tool and projects a certain extent from end 12, the maximum length of the projection is defined by the operating conditions and depend upon the tooth anatomy.

FIG. 3 shows a tool particularly adapted to be attached to a dental hand held tool (FIG. 6) which can be either mechanical or ultrasonic. The cavity 14 occupies the first portion 8 only partially and terminates therein in communication with a substantially cylindrical space 16, closed at its opposite end and having a bigger diameter than the cavity itself. The inside walls of the space 16 houses the upper end of core 15 against the action of a normal spring 16'; the upper end is provided with a preferably ball-shaped swelling 17 the dimensions of which are smaller than the inner dimensions of space 16 so that it gets engaged inside it and that a limited longitudinal elastic sliding path is defined therein for core 15, as well as an intermediate area between the swelling 17 and the inner walls of space 16 which is sufficient to make the swelling itself and therefore the core, independent of the rotation tool.

Practically this embodiment provides the possibility of removing and replacing the core 15 at the inside of the tool, either if it is worn or if it has to be replaced by other cores of different length, section and conformation. This can be accomplished as shown in FIG. 5. According to this solution the first portion 8 consists of two bodies adapted to be fitted together in a removable manner, one of which, identified at 18, is integral to the second operating portion 10 and the other, identified at 19, is free and susceptible of being engaged and locked to the preceding one by common means such as for example complementary screw threadings 20.

Each of the bodies 18 and 19 inwardly defines a portion of the space 16 and their mutual assembling reconstitutes the whole space, as shown in FIG. 3.

FIG. 4 shows the tool as adapted for manual operation which has a handle engaged with the upper end of the first portion 8. In this case, cavity 14 occupies both portions 8 and 10 over the whole length of the tool and houses the core 15. Core 15 projects not only from the free end 12 but also from the opposite end in the middle of handle 21. The end of core 15 concerned with handle 21 is in turn provided with a knob 22 for manual operation and is independent of the operation carried out by the tool.

The maximum length of core 15 coming out of end 12 can be, in this case, adjusted by the operator as well as the core itself can be pulled out of cavity 14 or introduced therein, when required. According to this embodiment the length 23 coming out of end 12 can be provided, over a certain portion starting from the end of the core, with some cutting and/or reaming means similar to means 11. In this way core 15, besides its main task consisting in guiding the tool progressively along the curved portions of canal 3, when operated independently, can execute a partial previous enlargement of the canal.

Advantageously the cutting and/or reaming means 11 is obtained by applying a uniform carbon diamond coating having an appropriate granulometry, which is particularly efficient in carrying out the rectification (indicated in hatched lines in FIGS. 1 and 6) and in attacking the edge of enamel 24 which is very hard.

Advantageously, the cutting and/or reaming means 11, of any type, can either be uniformly applied over the whole working portion 10 and connection piece 13 or be differentiated as to the type and to the particular characteristics and possibilities of cutting and reaming, so that they can be different in the connection piece 13 and in the working portion 10 and even along successive equal or unequal lengths of the same working portion 10.

FIG. 6 shows the final operating condition of the tool in question emphasizing the particular guiding function of the independent core 15; here the connection piece 13 of truncated conical form appears very useful for attacking the enamel 24 and carrying out a partial flaring of opening 25 in the pulp chamber 26.

The second working portion 10 of cylindrical or conical form, can be chosen according to the different working conditions and requirements.

A set of tools each of them reproducing one or more of the solution described above can be provided wherein the sizes and conformations of the working portions and the lengths of the core vary progressively.

Obviously the embodiments of the invention described above are not intended to comprise a limitation, and modifications can be carried out within the scope of the claims.

What is claimed is:

1. A rigid dental tool for reaming and rectifying dental canals, comprising a first rigid longitudinally extending attachment portion, said first attachment portion being adapted for attachment to a drive means, a second rigid operating portion extending longitudinally from said first rigid portion for a predetermined distance, said second portion having an outer surface and inner surface, appropriate cutting means being on a major portion of the outer surface, a longitudinal cavity being defined by said inner surface and formed along the longitudinal axis of said second portion and at least a part of the longitudinal axis of said first portion, means to connect a flexible core to said first portion, one end of said flexible core extending through the cavity of said second portion and being freely slidable within said cavity, one end of said flexible core projecting a predetermined amount beyond said second rigid portion, said longitudinal cavity terminating in said first portion, said first portion defining a substantially cylindrical space, said cylindrical space being larger than the longitudinal cavity and said longitudinal cavity extending therefrom, a swelling formed at the other end of said flexible core with said swelling being located in said cylindrical space, a normal spring being located in said cylindrical space biased against said swelling and walls of the second portion which define said cylindrical space, said swelling and said spring and said cylindrical space being a predetermined size to provide a limited longitudinal elastic sliding path for said flexible core as well as an intermediate area between said swelling and walls of said space sufficient to provide independent rotation between the tool and flexible core.

2. A rigid dental tool according to claim 1 wherein said first portion consists of two bodies, one of said bodies being integral with said second portion and being severably connected to the other body; and each of said bodies defining a part of the said longitudinal cavity formed in said first portion.

3. A rigid dental tool, according to claim 1, wherein a major part of said second operating portion is cylindrical.

4. A rigid dental tool, according to claim 1, wherein a major part of said second operating portion is conical with the diameter progressively decreasing away from said first portion.

5. A rigid dental tool, according to claim 1, wherein said cutting consist of a uniform carbon diamond coating having an appropriate granulometry.

6. A rigid dental tool according to claim 1 wherein reaming means replaces at least a portion of the cutting means on the surface of the second portion.

7. A rigid dental tool for reaming and rectifying dental canals, comprising a first longitudinally extending attachment portion, said first attachment portion being adapted for attachment to a drive means, a second rigid operating portion extending longitudinally from said first rigid portion for a predetermined distance, said second portion having an outer surface and inner surface, appropriate cutting means being on a major portion of the outer surface, a longitudinal cavity being defined by said inner surface and formed along the longitudinal axis of said second portion and at least a part of the longitudinal axis of said first portion, means to connect a flexible core to said first portion, one end of said flexible core extending through the cavity of said second portion and being freely slidable within said cavity, one end of said flexible core projecting a predetermined amount beyond said second rigid portion, said cylindrical cavity extends through said first and second portions, said core being sized to extend beyond both said first and second portions, a handle connected to that part of the core extending beyond said first portion, and said handle being mounted to provide independent manual rotation of the core, a cutting means attached to that part of said core extending beyond said second portion.

8. A rigid dental tool according to claim 7 wherein reaming means replaces at least a portion of the cutting means on the second portion and the part of the core extending beyond the second portion.

9. A rigid dental tool for reaming and rectifying dental canals, comprising a first rigid longitudinally extending attachment portion, said first attachment portion being adapted for attachment to a drive means, a second rigid operating portion extending longitudinally from said first rigid portion for a predetermined distance, said second portion having an outer surface and inner surface, appropriate cutting means being on a major portion of the outer surface, a longitudinal cavity being defined by said inner surface and formed along the longitudinal axis of said second portion and at least a part of the longitudinal axis of said first portion, means to connect a flexible core to said first portion, one end of said flexible core extending through the cavity of said second portion and being freely slidable within said cavity, one end of said flexible core projecting a predetermined amount beyond said second rigid portion, a stem connecting said first and second portions, said stem being frusto-conical with a base of bigger diameter corresponding to a lower section of said first portion and a base of smaller diameter corresponding to an upper section of said second operating portion, and said frusto-conical stem has cutting means on its outer surface.

10. A rigid dental tool, according to claim 9, wherein reaming means replaces at least a portion of the cutting means attached to the surface of the second portion and stem.

* * * * *